(12) United States Patent
Ohashi et al.

(10) Patent No.: US 11,191,782 B2
(45) Date of Patent: Dec. 7, 2021

(54) ANTI-TUMOR T CELLS AND THEIR PREPARATION USING IL-6

(71) Applicant: UNIVERSITY HEALTH NETWORK, Toronto (CA)

(72) Inventors: Pamela S. Ohashi, Toronto (CA); Michael St. Paul, Richmond Hill (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 203 days.

(21) Appl. No.: 16/478,787

(22) PCT Filed: Dec. 19, 2017

(86) PCT No.: PCT/CA2017/000270
§ 371 (c)(1),
(2) Date: Jul. 17, 2019

(87) PCT Pub. No.: WO2018/132889
PCT Pub. Date: Jul. 26, 2018

(65) Prior Publication Data
US 2020/0138862 A1 May 7, 2020

Related U.S. Application Data

(60) Provisional application No. 62/447,489, filed on Jan. 18, 2017.

(51) Int. Cl.
| | | |
|---|---|---|
| *A61K 35/17* | (2015.01) | |
| *A61K 38/20* | (2006.01) | |
| *A61P 35/00* | (2006.01) | |
| *C07K 14/525* | (2006.01) | |
| *C07K 14/54* | (2006.01) | |
| *C07K 14/705* | (2006.01) | |
| *C07K 16/24* | (2006.01) | |
| *C07K 16/28* | (2006.01) | |

(52) U.S. Cl.
CPC ............. *A61K 35/17* (2013.01); *A61P 35/00* (2018.01); *C07K 14/525* (2013.01); *C07K 14/5412* (2013.01); *C07K 14/70517* (2013.01); *C07K 16/247* (2013.01); *C07K 16/249* (2013.01); *C07K 16/2818* (2013.01); *C07K 14/5406* (2013.01)

(58) Field of Classification Search
CPC .............................. A61K 35/17; A61K 38/204
See application file for complete search history.

(56) References Cited

PUBLICATIONS

Hinrichs, Christian S. et al, Type 17 CD8+ T cells display enhanced antitumor immunity, American Society of Hematology, Blood 2009 114: pp. 596-599, Prepublished online May 26, 2009; DOI:10.1182/blood-2009-02-203935 Copyright 2011 by The American Society of Hematology; Washington DC 20036.
Kemp, Roslyn A.,et al, Tumor-Specific Tc1, But Not Tc2, Cells Deliver Protective Antitumor Immunity 1, The Journal of Immunology, 2001, 167, pp. 6497-6502, 0022-1767/01/$02.00.
Liu, Yun et al, Interleukin-21 induces the differentiation of human Tc22 cells via phosphorylation of signal transducers and activators of transcription, Immunlogy 132, pp. 540-548, Blackwell Publishing Ltd, DOI:10.1111/i.1365-2567.2010.03399.x.
Lu, Yong et al., Tumor-specific IL-9-producing CD8+ Tc9 cells are superior effector than type-I cytotoxic Tc1 cells for adoptive immunotherapy of cancers, article, PNAS Feb. 11, 2014, vol. 111, No. 6; pp. 2265-2270, www.pnas.org/cgi/doi/10.1073/pnas.1317431111.
Res, Pieter C.M., et al, Overrepresentation of IL-17A and IL-22 Producing CD8 T Cells in Lesional Skin Suggests Their Involvement in the Pathogenesis of Psoriasis, PLoS ONE, Nov. 2010;vol. 5; Issue 11;e14108 pp. 1-11, www.plosone.org.
Yu, Yu et al., Established Melanoma through Distinct Elicits Antitumor Immunity against Adoptive Transfer of Tc1 or Tc17 Cells Mechanisms, The Journal of Immunlogy, 2013; 190: pp. 873-1881; Prepublished online Jan. 11, 2013, DOI: 10.4049/jimmunol. 1201989, http://www.jimmunol.org/content/190/4/1873, Print ISSN: 0022-1767 Online ISSN 1550-6606.
PCT international Search Report and Written Opinion dated Apr. 2, 2018 re: International Application No. PCT/CA2017/000270.
Yang R et al. "IL-6 promotes the differentiation of a subset of naive CD8-T cells into IL-21-producing B helper CD8-T cells", Journal of Experimental Medicine, vol. 2I3(II); 2281-91; Sep. 21, 2016 (Sep. 21, 2016).
Liu et al.; "Interleukin-21 induces the differentiation of human Tc22 cells via phosphorylation of signal transducers and activators of transcription", Immunology, Apr. 2011, vol. 32, pp. 540-548.
Res PCM et al. "Overrepresenlation of IL-17A and IL-22 Producing CD8 T Cells in Lesional Skin Suggests Their Involvement in the Pathogenesis of Psoriasis", PLoS ON, 5(11):c14108; Nov. 24, 2010(Nov. 24, 2010).
Lim C et al., "The role of the 1L-22/IL-22RI axis in cancer", Cytokine & Growth Factor Reviews, 25(3):257-71; Jun. 2014 (Jun. 2014).
Yi P et al, "A tightly regulated IL-22 response maintains immune functions and homeostasis in systemic viral infection", Scientific Reports, 7(I):3857; Jun. 20, 2017 (Jun. 20, 2017).
Voigt C et al, "Cancer cells induce interleukin-22 production from memory CD4+ T cells via interleukin-1 to promote tumor growth", PNAS, 201705165: Nov. 17, 2017 (Nov. 17, 2017).
Kupper. Natascha Jennifer (2017): "Analysis of T cells as potential sources of interleukin-22 in colorectal cancer". Doctoral dissertation, Faculty of Medicine, Ludwig Maximilian University of Munich, Germany: presented Feb. 20, 2017: Deposited Mar. 8, 2017(Mar. 8, 2017), [Retrieved on Jan. 15, 2018 (Jan. 15, 2018)]. [Retrieved from: <URL https://edoc.ub.uni-muenchen.de/20475/].

*Primary Examiner* — Prema M Mertz
(74) *Attorney, Agent, or Firm* — Norton Rose Fulbright Canada LLP

(57) ABSTRACT

There is described herein a method for inducing Tc22 lineage T cells from a population of CD8+ T cells, the method comprising: a) providing a population of CD8+ T cells; b) activating the population of CD8+ T cells; and c) culturing or contacting the population of CD8+ T cells with IL-6.

12 Claims, 15 Drawing Sheets
Specification includes a Sequence Listing.

ANTI-TUMOR T CELLS AND THEIR PREPARATION USING IL-6

RELATED APPLICATION

This application claims priority to U.S. Provisional Application No. 62/447,489 filed on Jan. 18, 2018, herein incorporated by reference.

FIELD OF THE INVENTION

The invention relates to T-cells and specifically, to a IL-22+CD8+ T cell subset with anti-tumor function.

BACKGROUND OF THE INVENTION

The typical $CD8^+$ T cell is regarded as a highly cytotoxic cell type that produces large amounts of interferon (IFN)-γ. Studies over the past decade have challenged this notion by identifying distinct lineages of $CD8^+$ T cells, each producing a unique profile of cytokines and transcription factors, as well as displaying varying cytolytic capacities. The earliest subsets identified were the IFN-γ producing Tc1s and the $IL-4^+Tc2s$[1-4], while recent studies have expanded the $CD8^+$ T cell lineages to include the $IL-9^+Tc9s^{5,6}$ and the $IL-17^+$ Tc17s[7-11]. Each Tc subset differs in their killing capacities, with Tc1s being highly cytotoxic and Tc17s being poorly cytotoxic[9]. The polarization of Tc subsets is mediated by the same cytokines as their $CD4^+$ T-helper (Th) counterparts, involving different combinations of IL-4, IL-6, IL-12 and transforming growth factor (TGF)-β. Indeed, this also leads to the utilization of many of the same signaling pathways and transcription factors as their Th equivalents. For example, Tc17 polarization is dependent on the transcription factors RORγT, IRF4 and STAT3[9,12,13]. A variety of Tc subsets are generated in vivo during the immune response to infections and autoimmune diseases[5,8,13], and many different Tc subsets infiltrate several types of mouse and human tumors[11,14]. However, the precise physiological role of these Tc subsets remains to be fully elucidated.

IL-22 is a member of the IL-10 family of cytokines that acts on cells expressing IL-22R1, namely epithelial cells, keratinocytes, hepatocytes and pancreatic β cells. IL-22 helps to maintain the epithelial barrier by promoting tissue repair and wound healing, as well as to induce anti-microbial peptides and pro-inflammatory cytokines[15]. Although in some instances IL-22 can inhibit tumor growth[16,17] IL-22 is generally considered to be pro-tumorigenic by promoting inflammation as well as tumor cell proliferation and survival[18-20]. IL-22 is mainly produced by cells of lymphoid origin including innate lymphoid cells and T cells[21]. Recently, a novel subset of human $CD8^+$ $IL-22^+$ Tc22s was identified after examining the cytokine profile of $CD8^+$ T cells infiltrating psoriatic and atopic dermatitis lesions[22-24]. In addition to infiltrating inflamed skin lesions, Tc22s arise in response to HIV[25] and IL-22 producing $CD8^+$ T cells have also been shown to infiltrate squamous cell and hepatocellular carcinomas 26,27. Although the polarizing conditions for Tc22s have yet to be defined, it was found that IL-21 could induce IL-22 production in $CD8^+$ T cells[28]. However, it is unclear whether these cells are a distinct Tc22 lineage.

SUMMARY OF THE INVENTION

In an aspect, there is provided a method for inducing Tc22 lineage T cells from a population of CD8+ T cells, the method comprising: a) providing a population of CD8+ T cells; b) activating the population of CD8+ T cells; and c) culturing or contacting the population of CD8+ T cells with IL-6.

In an aspect, there is provided a population of cells comprising Tc22 lineage T cells that are CD8+/IL-22+/IL17-/IFNγlow.

In an aspect, there is provided a population of Tc22 lineage T cells produced by the method described herein.

In an aspect, there is provided the population described herein, for use in the treatment of cancer, preferably a cancerous tumor.

In an aspect, there is provided a method of treating cancer, preferably a cancerous tumor, in a patient, the method comprising administering to the patient the population described herein.

In an aspect, there is provided a use of the population described herein, in the manufacture of a medicament for the treatment of cancer, preferably a cancerous tumor.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1:
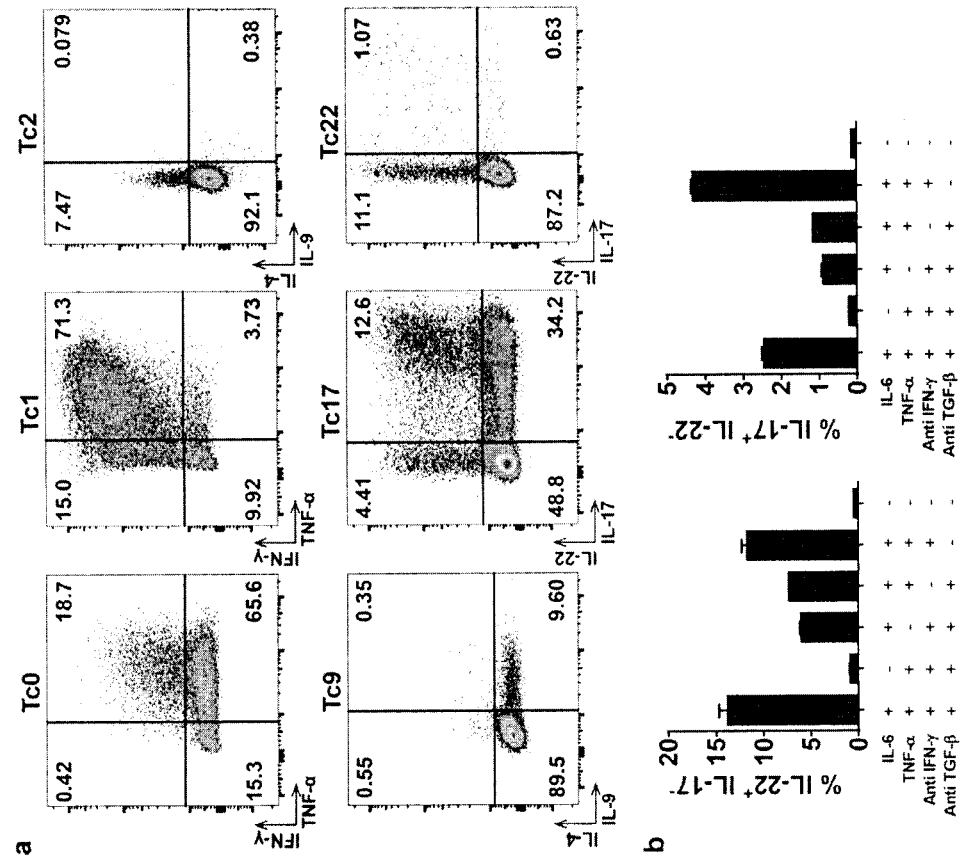
FIG. 1 shows IL-6 drives the polarization of $CD8^+$ IL-22 producing Tc22s. (a) Cytokine production was assessed in CD8+ T cells that were co-cultured with LPS-matured bone marrow-derived dendritic cells (BMDCs) for 3 days in the indicated polarizing conditions—Tc0: no cytokines, Tc1: IL-12, Tc2: IL-4+anti-IFN-γ, Tc9: IL-4+TGF-β+anti-IFN-γ, Tc17: IL-6+IL-23+TGF-β+anti-IFN-γ, Tc22: IL-6+TNF-α+FICZ+anti-TGF-β+anti-IFN-γ. All dot plots shown are gated on CD8+ T cells. (b) CD8+ T cells were stimulated with the indicated cytokines and neutralizing antibodies. When IL-6 or TNF-α were omitted from the culture conditions, a corresponding cytokine neutralizing antibody was added instead. Graphs represent mean % of IL-22+IL-17-CD8+ T cells±standard error of technical replicates. Data shown is representative of at least 2-3 independent experiments.

In the following description, numerous specific details are set forth to provide a thorough understanding of the invention. However, it is understood that the invention may be practiced without these specific details.

In one aspect, the present invention is directed to stimulation, activation, or expansion of T cells, including but not limited to CD4+ and CD8+ T cells.

CD8+ T cells can be polarized into several different subsets as defined by the cytokines they produce and the transcription factors that govern their differentiation. The polarizing conditions to induce a novel IL-22 producing CD8+Tc22 subset were identified, which in an embodiment is dependent on IL-6 and preferably aryl hydrocarbon receptor transcription factor. Further characterization showed that this subset is highly cytolytic and expresses a distinct cytokine profile as well as a unique transcriptome relative to other subsets. In addition, polarized Tc22 were able to control tumor growth as well as or if not better than the traditional IFN-γ producing Tc1 subset. With these anti-tumor properties, it may be attractive to polarize T cells to the Tc22 lineage when using CAR-T or TCR transduction based immunotherapies.

In an aspect, there is provided a method for inducing Tc22 lineage T cells from a population of CD8+ T cells, the method comprising: a) providing a population of CD8+ T cells; b) activating the population of CD8+ T cells; and c) culturing or contacting the population of CD8+ T cells with IL-6.

Methods of activating T cells are known in the art, for example, as described in T Cell Activation, Annu. Rev. Immunol. 2009. 27:591-619.

The term "activation", as used herein, refers to the state of a cell following sufficient cell surface moiety ligation to induce a noticeable biochemical or morphological change. Within the context of T cells, such activation refers to the state of a T cell that has been sufficiently stimulated to induce cellular proliferation. Activation of a T cell may also induce cytokine production and performance of regulatory or cytolytic effector functions. Within the context of other cells, this term infers either up or down regulation of a particular physico-chemical process The term "activated T cells" indicates T cells that are currently undergoing cell division, cytokine production, performance of regulatory or cytolytic effector functions, and/or has recently undergone the process of "activation."

In some embodiments, the activation comprises culturing or contacting the population with at least one of (i) anti-CD3 antibody and (ii) gp33 peptide from LCMV (SEQ ID NO. 1:KAVYNFATM).

In some embodiments, the population of CD8+ T cells is additionally cultured or contacted with TNF-α or IL-6.

In some embodiments, the population of CD8+ T cells is additionally cultured or contacted with an aryl hydrogen receptor (AhR) agonist, preferably 6-Formylindolo(3,2-b) carbazole (FICZ). A number of other AhR agonists are known, such as those described in Mol. Cell. Biol. May 2014 vol. 34 no. 9 1707-1719.

In some embodiments, the population of CD8+ T cells is additionally cultured or contacted with anti-IFNγ antibody.

In some embodiments, the population of CD8+ T cells is additionally cultured or contacted with anti-TGF-β antibody.

In some embodiments, the population of CD8+ T cells is additionally cultured or contacted with IL-21.

In some embodiments, the population of CD8+ T cells is additionally cultured or contacted with IL-23.

In some embodiments, the Tc22 lineage T cells are CD8+/IL-22+/IL17-/IFNγlow.

In some embodiments, the Tc22 lineage T cells are additionally IL-4-, IL-5-, IL-9-, IL-10- and/or or IL-13-, and preferably are additionally TNF-αhi and/or IL-2hi.

In some embodiments, step c) is performed before or after step b). In other embodiments, step c) is performed simultaneously with step b).

In an aspect, there is provided a population of cells comprising Tc22 lineage T cells that are CD8+/IL-22+/IL17-/IFNγlow.

In an aspect, there is provided a population of Tc22 lineage T cells produced by the method described herein.

In an aspect, there is provided the population described herein, for use in the treatment of cancer, preferably a cancerous tumor.

In an aspect, there is provided a method of treating cancer, preferably a cancerous tumor, in a patient, the method comprising administering to the patient the population described herein.

In an aspect, there is provided a use of the population described herein, in the manufacture of a medicament for the treatment of cancer, preferably a cancerous tumor.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The T cell populations generated herein would be understood to beneficial in treating cancer, and may include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, and wilms tumor.

The advantages of the present invention are further illustrated by the following examples. The examples and their particular details set forth herein are presented for illustration only and should not be construed as a limitation on the claims of the present invention.

EXAMPLES

Methods and Materials

Mice and Tumors—

C57BL/6, AhR floxed with CD4 cre (referred to as AhR$^{-/-}$) and Tbet$^{-/-}$ mice were purchased from the Jackson Laboratory and Taconic. Generation of P14 mice, which express a transgenic TCR specific for the gp33 peptide of the lymphocytic choriomeningitis virus (LCMV) and H-2D$^b$ was described previously[45]. 8-12 week old B6 mice were inoculated subcutaneously with $4 \times 10^5$ B16F10-gp33. 10-11 days later, mice bearing tumors of ~5 mm diameter were randomly allocated to different treatment groups, some of which received $1 \times 10^6$ polarized CD8$^+$ P14 T cells i.v. Tumor size was continually assessed using calipers until mice reached experimental endpoint (diameter ≥1.5 cm or severe ulceration/necrosis). Upon death, mice were given a tumor size of 225 mm$^2$ representing the maximum endpoint value of 1.5 cm×1.5 cm, or given their last tumor measurement, whichever value is greater. All mice were maintained at the Ontario Cancer Institute animal facility according to institutional guidelines and with approval of the Ontario Cancer Institute Animal Ethics Committee.

Tc Subset Polarization—

CD8$^+$ T cells were magnetically purified (Miltenyi Biotec) from P14 and non-P14 mice and co-cultured either with mature bone marrow dendritic cells (BMDCs) pulsed with gp33 peptide from LCMV (KAVYNFATM)[46], or cultured with mature BMDCs+α-CD3 (145-2C11-1 μg/mL) for three days in IMDM supplemented with 10% FCS, L-glutamine, β-mercaptoethanol, penicillin and streptomycin. To generate Tc subsets, polarizing cocktails were added at the start of the co-culture as follows—Tc0: no additional cytokines, Tc1: IL-12 (5 ng/mL), Tc2: IL-4 (20 ng/mL)+anti-IFN-γ (XMG1.2-10 μg/mL), Tc9: IL-4 (10 ng/mL)+TGF-81 (10 ng/mL)+α-IFN-γ (10 μg/mL) and Tc17: IL-6 (20 ng/mL)+TGF-81 (3 ng/mL)+IL-23 (10 ng/mL)+α-IFN-γ (10 μg/mL). Tc22s were polarized with IL-6 (20 ng/mL)+TNF-α (40 ng/mL)+6-Formylindolo(3,2-b)carbazole (FICZ at 2 ng/mL)+α-IFN-γ (10 μg/mL)+α-TGF-β (1D11.16.8-10 μg/mL). On day 3 post-stimulation, cells were stained for flow cytometry or used for functional assays. Cytokines and neutralizing antibodies were purchased from Biolegend, eBioscience and R&D. FICZ and CH-223191 (used at 500 ng/mL) were purchased from Enzo Life Sciences and EMD Millipore, respectively.

Flow Cytometry—

Antibodies for flow cytometry were purchased from eBioscience, Biolegend, R&D, Life Technologies and BD Pharmingen. For intracellular cytokine staining, cells were re-stimulated for 6 hours with Cell-Stimulation Cocktail (eBioscience) in the presence of Brefeldin A (eBioscience), followed by staining using Cytofix/Cytoperm (BD Pharmingen) or Fixation/Permeabilization Buffer Set (eBioscience). In some instances, a fixable viability dye and Fc block were used (eBioscience). Phosphlow was performed using BD Phosflow Perm Buffer III on T cells that had been stimulated for 30 minutes in polarizing conditions. Flow cytometry data was acquired on a FACSCanto II (BD) and analyzed using FlowJo software (Tree Star).

RNA Sequencing—

RNA was extracted from day 3 polarized Tc subsets using RNeasy Mini Kit (Qiagen) according to manufacturer's instructions. RNA libraries were then prepared using TruSeq Stranded Total RNA kit with ribosomal RNA being depleted using Ribo-zero Gold rRNA beads. The cleaved RNA fragments were copied into first strand cDNA using reverse transcriptase and random primers. This is followed by second strand cDNA synthesis using RNase H and DNA Polymerase I. A single "A" based were added and adapter ligated followed by purification and enrichment with PCR to create cDNA libraries. Final cDNA libraries were size validated using Agilent Bioanalyzer and concentration validated by qPCR. All libraries were normalized to 10 nM and pooled together. 10 pM of pooled libraries were loaded onto Illumina cBot for cluster generation. Clustered flow cell was then sequenced Pair-end 100 cycles V3 using Illumina HighSeq 2000 to achieve ~30 million reads per sample. Tophat (2.0.8b)[47] software suite with Bowtie (2.0.5)[48] was used to align reads to the *Mus musculus* mm10 mouse genome (igenome). RNAseq (1.1.7)[49] was used to assess the quality of the aligned data and depletion based on median coverage across transcript length and identities of top expressed transcripts. Samtools (0.1.18)[50] was used to merge aligned technical replicates and sort alignment files. The cufflinks (2.2.1)[51] software suite was used to quantify alignments. Cuffquant was used to quantify individual sample alignments and Cuffnorm was used to normalize quantified data for each group of biological replicates. Cuffdiff was used in conjunction with the R (3.2.2)[52] library CummeRbund (2.10.0)[53] to explore the data at replicate and grouping levels and to generate dendogram and gene matrix figures. A custom python script was used to subset data based on an FPKM threshold of 1, and to apply additional thresholds as indicated.

Real-Time PCR—

RNA was reverse transcribed into cDNA using qScript cDNA Super Mix (Quanta) and gene expression was quantified by real-time PCR using PerfeCTa SYBR Green FastMix (Quanta) on the Applied Biosystems 7900HT using recommended parameters. Gene expression for all experiments were normalized to the house keeping gene GAPDH and expressed as fold change relative to Tc0.

Cytotoxicity Assay—

The cytotoxicity assay was performed as previously described[5]. Briefly, EL4 cells were pulsed with gp33 peptide from LCMV or a control adenovirus (AV) peptide (SGPSNTPPEI) for 2 hours. Gp33 pulsed cells were labelled with 10 μm CFSE and AV pulsed EL4 cells were labelled with 1 μm CFSE and mixed together at a 1:1 ratio. The mixture of EL4 cells were incubated with polarized Tc subsets expressing the P14 transgenic TCR for ~5 hours, and killing was assessed by measuring the ratio of high CFSE expressing cells to low CFSE expressing cells by flow cytometry.

Cytokine Quantification—

Polarized Tc subsets were re-stimulated for 24 hours with α-CD3 (1 ug/mL). Supernatants were collected after 24 hours and cytokine levels were quantified using LEGENDplex (Biolegend) or by ELISA (eBioscience).

Human Tissue and Blood Specimens—

Fresh tumor tissue was obtained from patients with ovarian cancer undergoing standard-of-care surgical procedures. Tissues were obtained from the UHN Biospecimen Sciences Program. Peripheral blood mononuclear cells were obtained from healthy donors. Tissue and blood were obtained through protocols approved by the institutional review board. Written informed consent was obtained from all donors who provided the samples.

Human Tc22 Polarization—

Fresh or cryopreserved PBMCs from healthy donors were thawed and magnetically sorted for naïve T cells (Miltenyi Biotec) and seeded into a 96-well plate previously coated with 5 μg/mL anti-CD3 (eBioscience, clone OKT3). To induce Tc22 polarization, the following antibodies and cytokines were added to culture: 1 μg/mL anti-CD28 (eBioscience, clone CD28.2), 5 μg/mL anti-IFNγ (Biolegend, clone B27), 5 μg/mL anti-IL-4 (Biolegend, clone 8D4-8), 5 μg/mL anti-TGFβ (eBioscience, clone 1D11.16.8), 20 ng/mL IL-6, 10 ng/mL IL-21, 10 ng/mL IL-23, 40 ng/mL TNF-α and 2 ng/mL FICZ (Enzo Life Sciences). Five days later, cells were stimulated with PMA/ionomycin (eBioscience)+Brefeldin A (eBioscience) for 5-6 hours. Cells were then stained and analyzed for intracellular cytokines by flow cytometry.

Ovarian Tumor-Infiltrating Lymphocyte (TIL) Staining—

Ovarian cancer TILs were expanded in IL-2 as previously described[54]. Cryopreserved ovarian TILs were thawed and rested for several days in IMDM (Hyclone) supplemented with 10% human serum (Gemini) and 1000 CU/mL IL-2 (Novartis). TILs were then re-stimulated with PMA/ionomycin (eBioscience)+Brefeldin A (eBioscience) for 5-6 hours. Cells were subsequently stained and analyzed for intracellular cytokines by flow cytometry.

Statistical Analysis—

Statistical analysis was performed using repeated measures ANOVA with sidak test for tumor growth curves and a Log-Rank test for survival curves and considered statistically significant when $p<0.05$.

Results and Discussion

IL-6 is the Driving Cytokine for Tc22 Polarization

Figure 7:
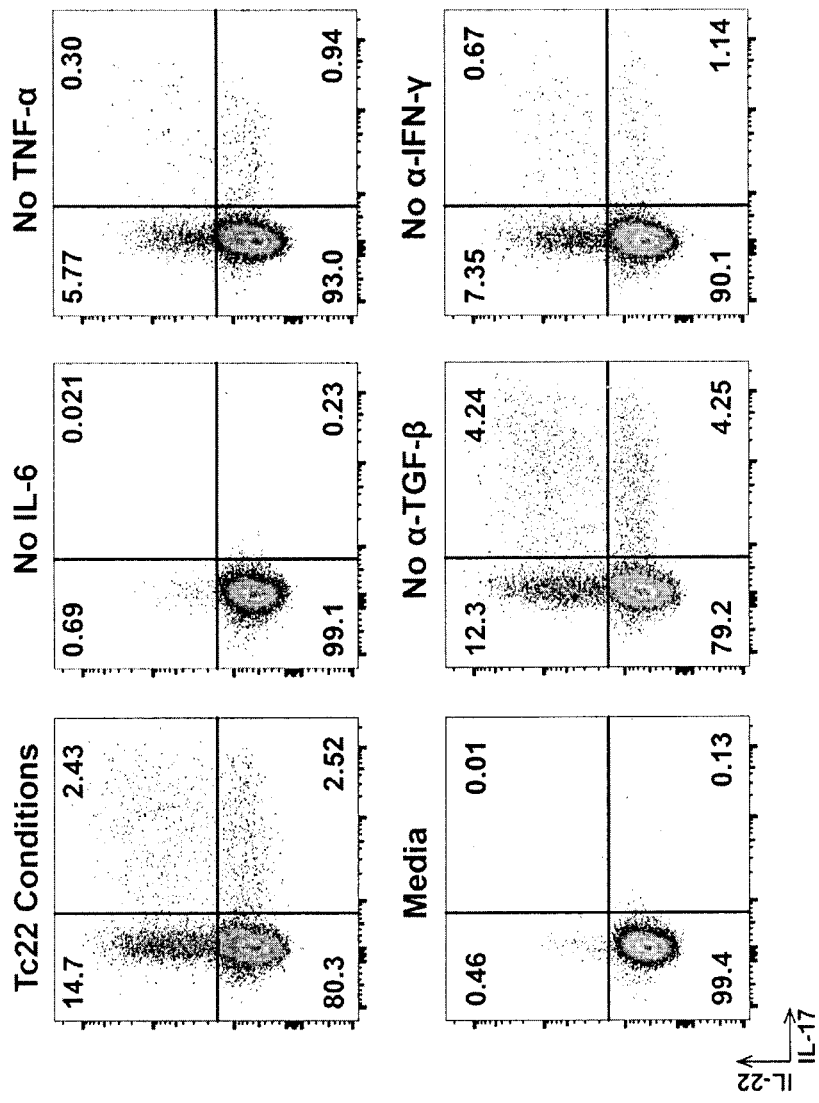
FIG. 7 shows Tc22 polarization is driven by IL-6. $CD8^+$ T cells were polarized in Tc0 conditions (media), in full Tc22 conditions or in Tc22 conditions lacking the indicated cytokines or neutralizing antibodies. When IL-6 or TNF-α were removed from the culture conditions, a corresponding cytokine neutralizing antibody was added in its place. All dot plots shown are gated on $CD8^+$ T cells. Results shown are representative of at least 2 independent experiments.

To establish our culture conditions used to polarize different CD8$^+$Tc subsets, we stimulated CD8$^+$ T cells in the presence of the previously defined polarizing conditions to induce Tc1s, Tc2s, Tc9s and Tc17s, or without any additional cytokines to generate Tc0s (FIG. 1A). Using the polarizing conditions for CD4$^+$Th22s as our starting point[29,30], we were able to induce a population of IL-22$^+$Tc22s that minimally expressed the other lineage-defining cytokines such as IFN-γ, IL-4, IL-9 and IL-17 (FIG. 1A). Tc22 polarization was dependent on IL-6, and further enhanced when combined with TNF-α and the aryl hydrocarbon receptor (AhR) agonist 6-Formylindolo (3,2-b) carbazole (FICZ), in conjunction with neutralizing antibodies for IFN-γ and TGF-8 (FIG. 1B, FIG. 7).

Tc22 Polarization is Inhibited by T-Bet and Facilitated by AhR

Transcription factors such as T-bet, RORγt (RORC) and AhR play a critical role in driving CD4$^+$Th polarization[31].

Figure 2:
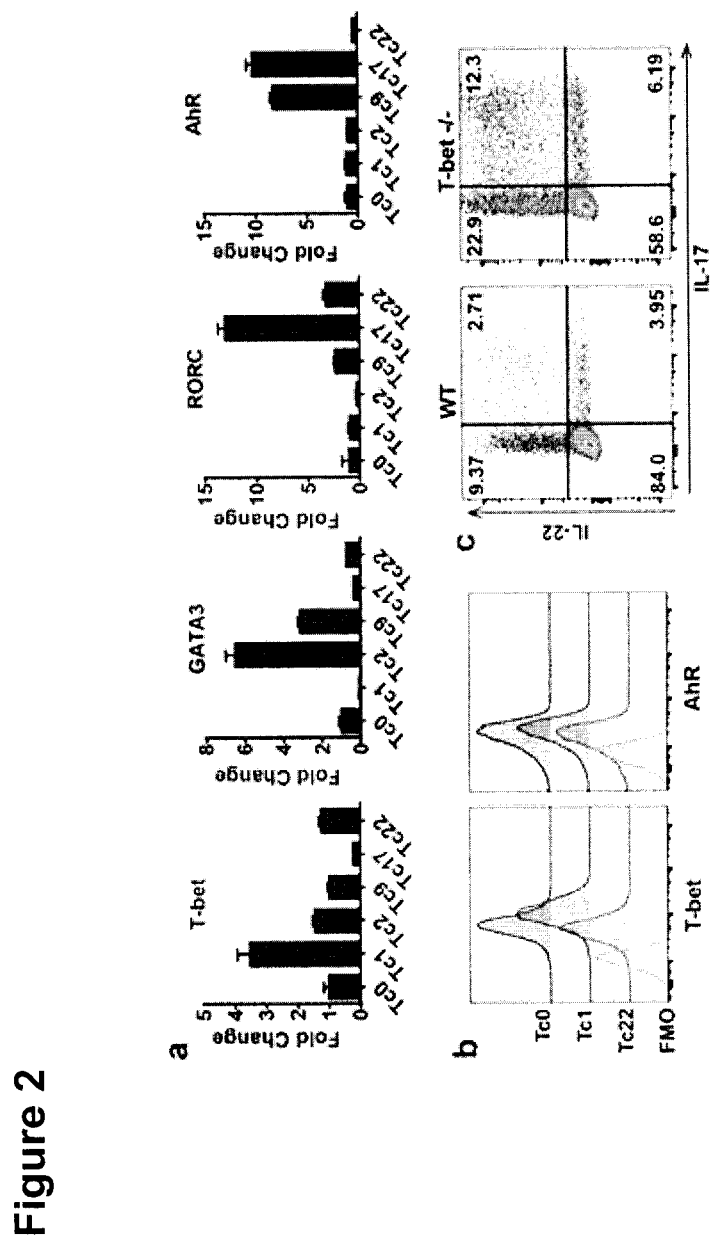
FIG. 2 shows Tc22 polarization is inhibited by T-bet and facilitated by AhR. (a) Gene expression in polarized Tc subsets expressed as fold change relative to Tc0. (b) AhR and T-bet expression levels in Tc0, Tc1 and Tc22s as determine by flow cytometry (c) WT and $T\text{-}bet^{-/-}$ CD8+ T cells were stimulated in Tc22 polarizing conditions for 3 days and cytokine production was assessed. (d) % IL-22 positive WT or $T\text{-}bet^{-/-}$CD8+ T cells stimulated for 3 days in the indicated polarizing conditions. (e) WT and $AhR^{-/-}$ CD8+ T cells were stimulated in Tc22 polarizing conditions for 3 days and cytokine production was assessed. (f) CD8+ T cells were stimulated in the presence of Tc22 polarizing conditions without FICZ. Either an AhR Antagonist (CH-223191-500 ng/mL), an AhR agonist (FICZ—2 ng/mL) or vehicle control were added at the start of the culture and cytokine production was assessed 3 days later. (g) % IL-22 positive CD8+ T cells after a 3 day stimulation in the indicated polarizing conditions in conjunction with CH-223191, vehicle control or FICZ. All FACs plots shown are gated on CD8+ T cells. Results are representative of at least 2-3 independent experiments.
Figure 2:
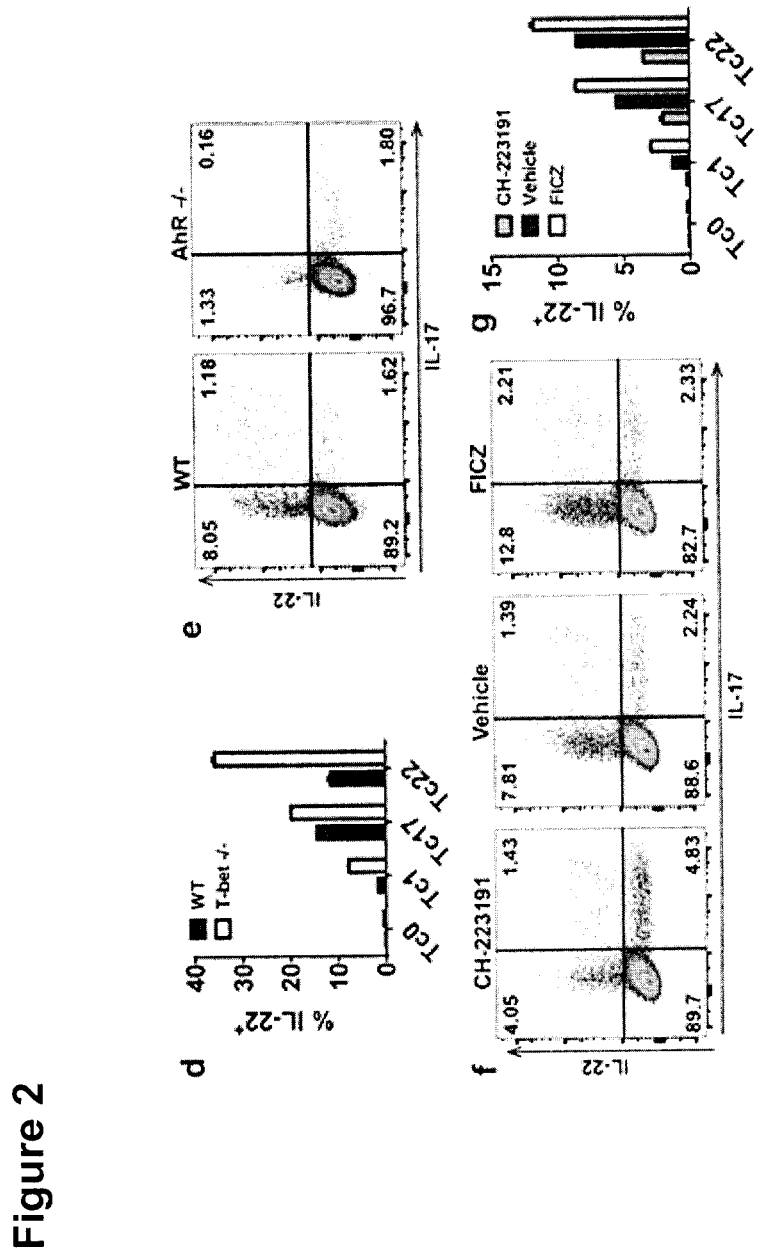
Figure 8:
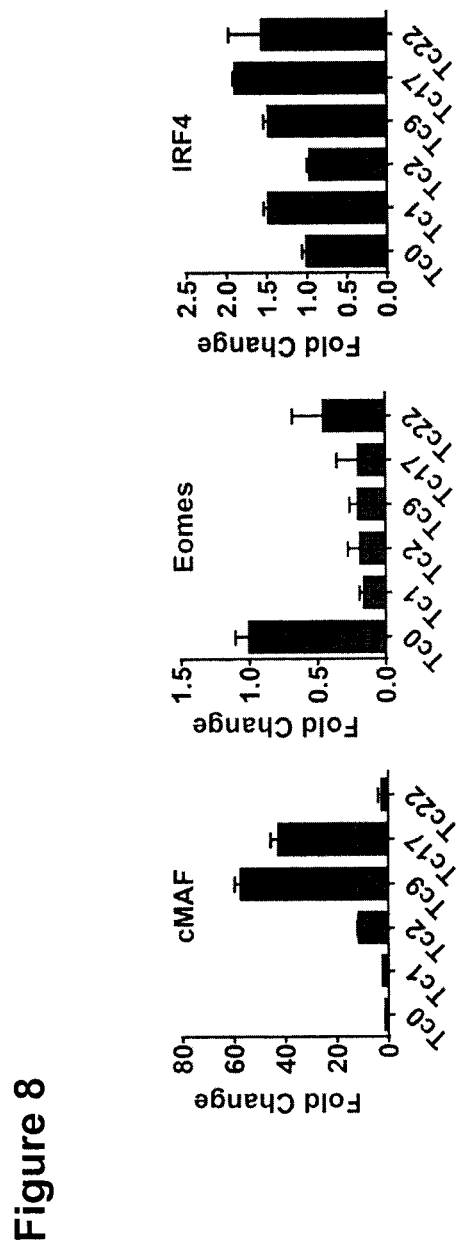
FIG. 8 shows transcription factor expression in Tc subsets. RNA was extracted from D3 polarized Tc subsets and gene expression was determined using real-time PCR. Values are expressed as fold change relative to Tc0.

Each defined Th subset has been found to have one or more "master regulator" transcription factors that are essential for their differentiation. When looking at the CD8+Tc subsets, we found that they differentially express many of these transcription factors in a manner similar to their CD4+ counterparts (FIG. 2A, FIG. 8). Of note, Tc1s had the highest T-bet transcripts, Tc2s had the highest GATA3 transcripts, and Tc17s had the highest expression of RORγt.

Figure 9:
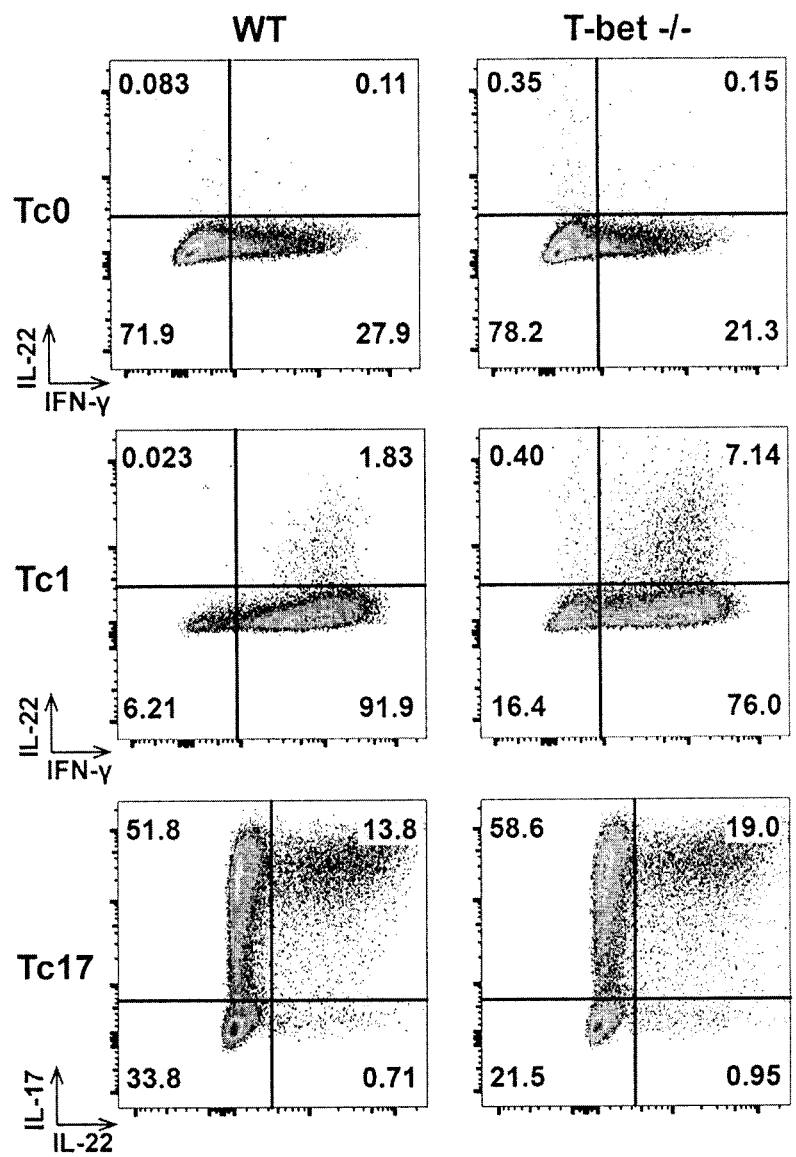
FIG. 9 shows role of T-bet in Tc Subset Polarization. WT or T-bet−/−CD8+ T cells were stimulated in Tc0, Tc1 or Tc17 polarizing conditions for 3 days and cytokine production was assessed. Plots shown are gated on CD8+ T cells.
Figure 10:
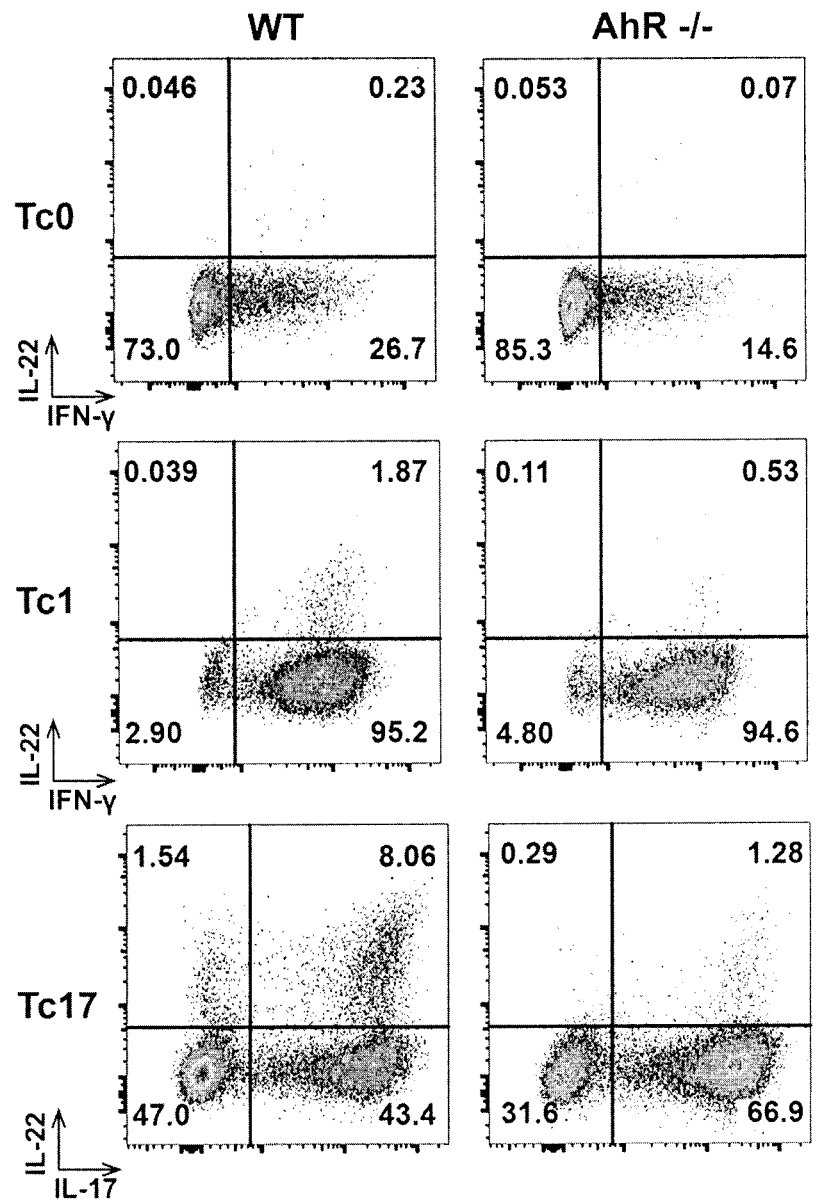
FIG. 10 shows role of AhR in Tc Subset Polarization. WT or AhR CD8+ T cells were stimulated in Tc0, Tc1 or Tc17 polarizing conditions for 3 days and cytokine production was assessed. Plots shown are gated on CD8+ T cells.
Figure 11:
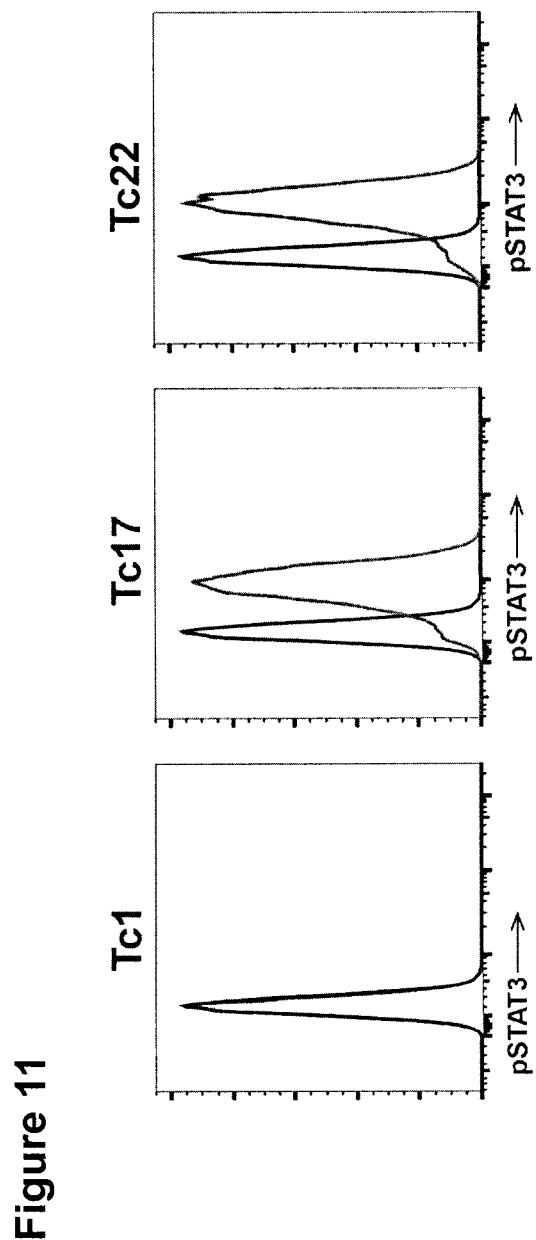
FIG. 11 shows phosphorylated STAT3 in Tc subsets. CD8+ T cells were stimulated for 30 minutes in Tc0 (black) or Tc1/Tc17/Tc22 (red) polarizing conditions and phospho-STAT3 levels were quantified by flow cytometry. All FACs plots shown are gated on CD8+ T cells.

The transcriptional control of Th22 polarization is thought to be dependent on T-bet and AhR, although Th22s demonstrate minimal expression of AhR transcripts[32]. Our data show that Tc22s express comparable amounts of AhR to Tc1s and Tc0s at the transcript and protein level, but less T-bet than either of these subsets (FIG. 2A,B). To determine whether T-bet was important for the development of the Tc22 lineage, we stimulated T-bet$^{-/-}$ CD8+ T cells in the presence of polarizing cytokines and found that T-bet$^{-/-}$ Tc0, Tc1, Tc17 and Tc22s all had enhanced IL-22 expression, indicating that T-bet is a negative regulator of IL-22 production in CD8+ T cells (FIG. 2C,D and FIG. 9). To evaluate the importance of AhR in Tc22 differentiation, we induced Tc subsets using AhR$^{-/-}$ CD8+ T cells and found IL-22 production to be markedly reduced (FIG. 2E). AhR also regulates IL-22 production in other subsets, as AhR TcOs, Tc1s, and Tc17s produced less IL-22 (FIG. 10). Moreover, Tc22 polarization was enhanced in the presence of the AhR agonist FICZ, or inhibited by the AhR antagonist CH-223191 (FIG. 2F). These effects were not limited to Tc22s, since treatment of Tc1s and Tc17s with FICZ and CH-223191 also promoted or inhibited IL-22 production, respectively (FIG. 2G). It is important to note, however, that AhR alone is not sufficient to induce IL-22 production and Tc22 polarization; virtually no increase in IL-22 production was observed in TcOs treated with FICZ alone. It is likely other transcription factors down-stream of IL-6 signaling are required such as STAT3, which we identified to be highly expressed in Tc22s compared to Tc0/Tc1s (FIG. 11). Collectively, these data demonstrate that IL-6 in conjunction with AhR drives IL-22 production and Tc22 differentiation.

Tc Subsets Display Unique Transcriptomes

Figure 3:
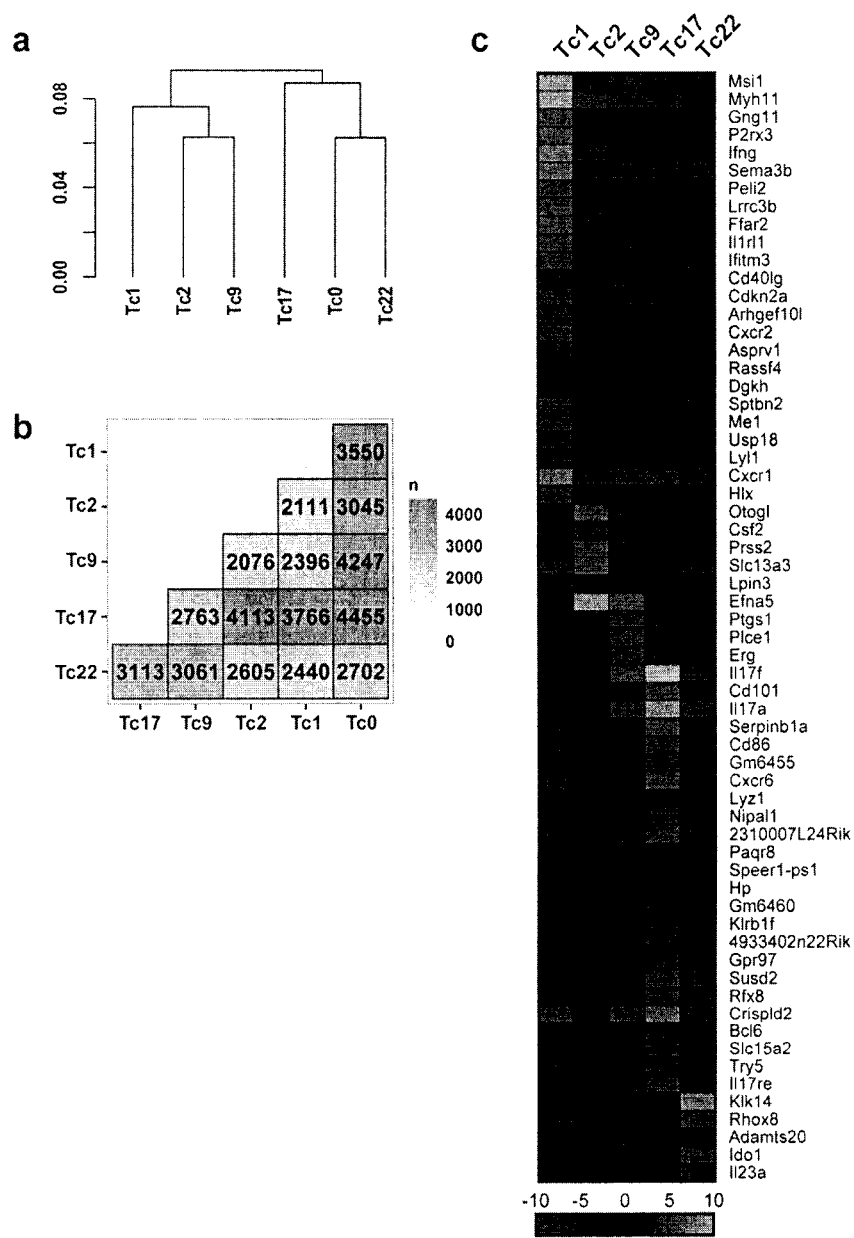
FIG. 3 shows Tc subset-specific transcriptional profiling. RNA was extracted from polarized CD8+Tc subsets from 3 different biological replicates and sequenced. (a) Dendrogram of Tc lineages. (b) Matrix of significant genes (p=0.05) of Tc lineages. (c) Heatmap showing transcriptional expression (log 2 Fold Change vs Tc0) of genes that are differentially expressed from Tc0 (fold Tc0>2) and that have lineage-specific upregulation (fold all others >4).

To assess the degree of similarity between Tc22s and other Tc subsets, we evaluated the transcriptome of CD8+Tc subsets using RNA sequencing (FIG. 3). We found that the Tc subsets can be divided into two clusters—one containing TcOs, Tc17s and Tc22s, and the other cluster containing Tc1, Tc2s and Tc9s (FIG. 3A). This clustering analysis indicated that Tc22s are most related to TcOs, which together are most related to Tc17s; while Tc2s are most related to a Tc9s, which together are most related to Tc1s. When looking solely at the absolute number of significantly different genes between each of the subsets, Tc17s were shown to have the greatest number of different genes when compared against the majority of Tc subsets (FIG. 3B). With respect to Tc22s, they were shown to have the least number of significantly different genes when compared against Tc1s, and the greatest number when compared to Tc17s. Nevertheless, when considering any permutation of comparisons between any of the Tc subsets, there were a minimum of at least 2000 significantly different genes, thereby indicating that each Tc subset is a distinct lineage.

To define a transcriptional signature of each Tc subset, we identified which genes were specific to each Tc lineage (FIG. 3C). Using the cutoff of genes being at least 4 fold up-regulated from any other subset, we identified lineage-specific genes for each Tc subset, some of which were for surface markers, transcription factors and cytokines. For example, IL-17A, CD101 and CD86 were found to be specific for the Tc17 lineage, while high IFNG was found to be indicative of Tc1s. In the case of Tc22s, five genes were identified—K1k14, Rhox8, Adamts20, Ido1 and IL23A.

Tc Subsets Differentially Express Surface Markers

Figure 4:
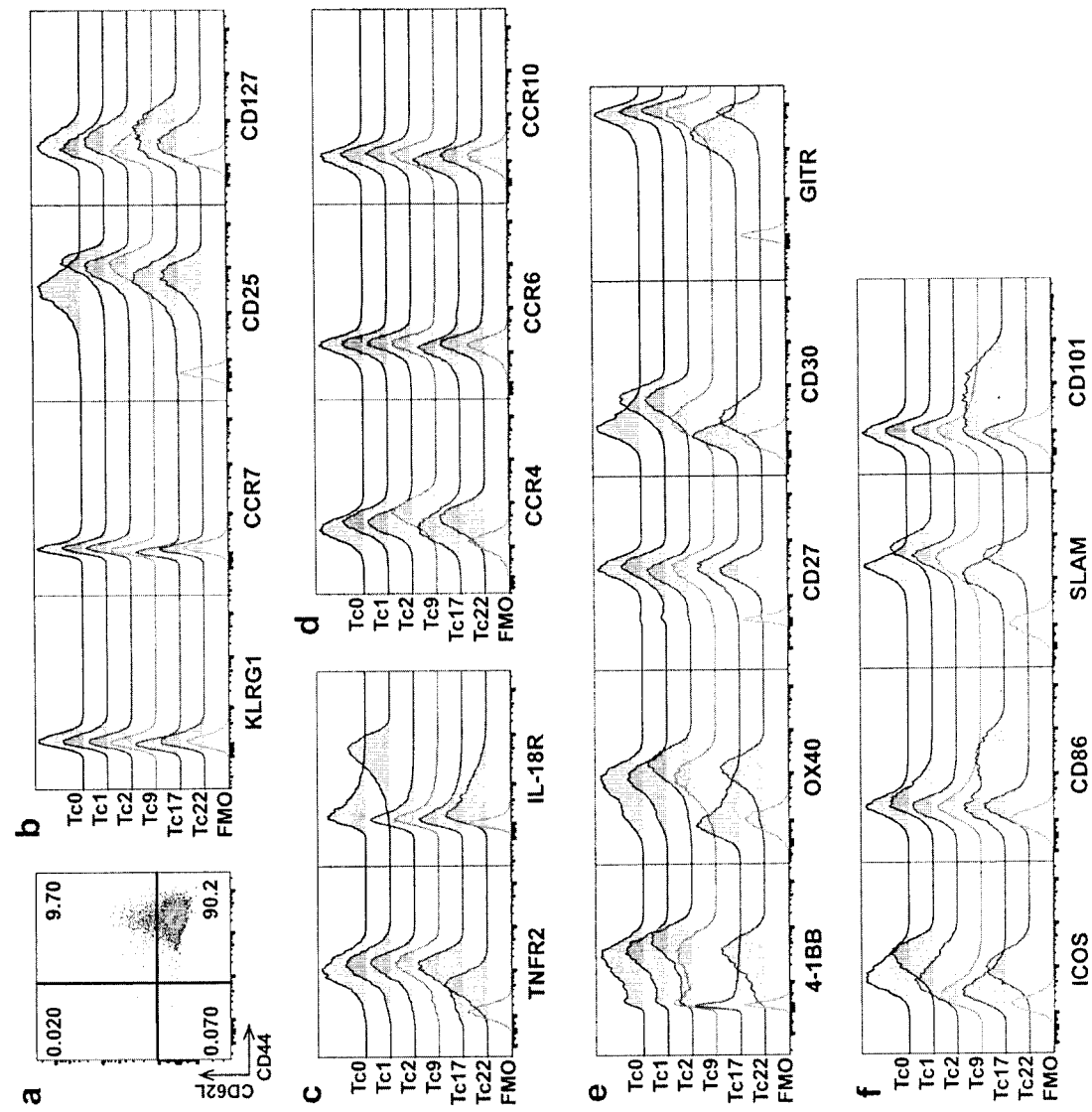
FIG. 4 shows Tc subsets differentially express surface markers. CD8+ T cells were stimulated for 3 days in Tc polarizing conditions and surface markers were analyzed by flow cytometry: (a) CD62L and CD44 expression on TcOs (b) KLRG1, CCR7, CD25 and CD127 (c) TNFR2 and IL-18R, (d) CCR4, CCR6 and CCR10 (e) TNF-superfamily members 4-1BB, OX40, CD27, CD30 and GITR and (f) Co-stimulatory molecules ICOS, CD86, SLAM and CD101. All plots shown are gated on CD8+ T cells. Results are representative of at least 2-3 independent experiments.

Next, we evaluated the activation status of each of the polarized CD8+Tc subsets by examining the expression of several different markers by flow cytometry. All Tc subsets had a similar effector phenotype, as they were CD44$^{hi}$/CD62L$^-$/CCR7$^-$/KLRG1$^-$ in addition to expressing high levels of CD25 and low levels of CD127 (FIGS. 4A,B).

An important aspect of defining and characterizing different CD8+ T cell lineages is finding unique surface markers expressed by each subset to facilitate their identification. In addition to examining markers commonly used to identify CD4+Th subsets, we also explored the RNA seq data to look for novel identifying markers. Together, this led us to investigate several types of surface molecules including cytokine receptors (FIG. 4C), chemokine receptors (FIG. 4D) and co-stimulatory molecules (FIGS. 4E,F). In the case of cytokine receptors, minimal differences in IL-6R, IL-23R, TNFR1, IL-4R and IL-21R expression were observed amongst the subsets (data not shown). The best uniquely identifying cytokine receptor we found was IL-18R, which RNA seq analysis revealed as being highly expressed by Tc1s. We subsequently validated this by flow cytometry and observed a similar pattern—all of the subsets were IL-18R$^{lo}$ while Tc1s were IL-18R$^{hi}$ (FIG. 4C). For Tc22s, we did not identify a unique cytokine receptor, however, Tc22s did express lower levels of TNFR2 compared to all of the other subsets (FIG. 4C). When looking at the expression levels of different chemokine receptors, we found that CCR6, CCR10, CXCR1, CXCR2, CXCR3 and CXCR5 were either expressed at low levels, or expressed but with minimal differences amongst the subsets (FIG. 4D and data not shown). The only exception was CCR4, which was highly expressed on Tc9s compared to other Tc subsets. In general however, unlike the CD4+T helper counterparts, differential expression of the chemokine receptors were unable to discriminate between the various CD8+Tc subsets.

Next, we investigated the expression of co-stimulatory markers, as several have been shown to be differentially expressed on CD4+T helper subsets[33]. Many differences in expression were observed amongst the various subsets, however the most striking differences were found in the expression of 4-1BB and OX40. These markers were both highly expressed on all of the Tc subsets except for Tc17s, which surprisingly did not express either molecule (FIG. 4E). In addition Tc17 cells also expressed lower levels of CD30 and GITR compared to other Tc subsets. In contrast, Tc17s expressed both CD86 and CD101 at high levels, both of which were identified by RNA seq as being specific to Tc17s (FIG. 4F). In the case of Tc1s and Tc22s, both of these subsets expressed high levels of ICOS but could be distinguished from each other based on the high IL-18R expression by Tc1s and not Tc22s. Together, these results show that co-stimulatory markers are differentially expressed amongst subsets, with Tc17s standing out from the rest of the Tc subsets with respect to the majority of markers examined.

Tc Subsets have Distinct Cytokine Profiles and Cytolytic Activity

Figure 5:
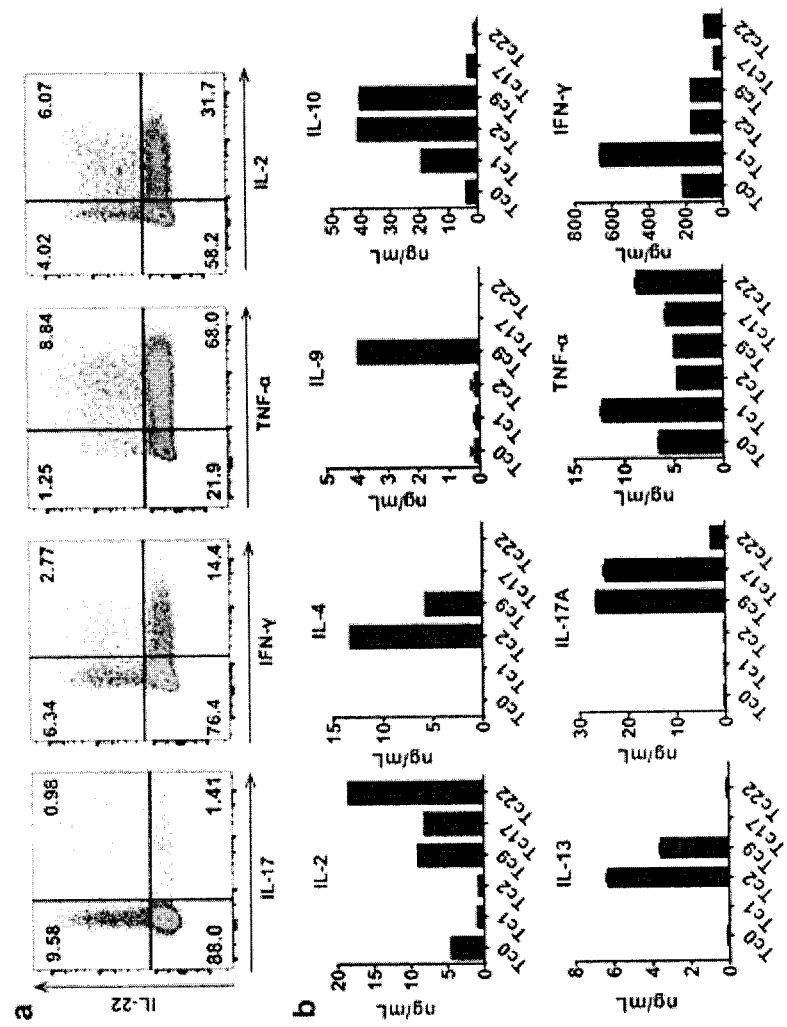
FIG. 5 shows Tc subsets have distinct effector functions. (a) CD8+ T cells were stimulated for 3 days in Tc22 polarizing conditions and ICS was performed after a 6 hour re-stimulation. (b) Cytokine levels in supernatants in Tc subsets after a 24 hour re-stimulation with anti-CD3. Results are means of technical replicates±standard error. (c) IL-22 expression in TcOs, Tc1s, Tc2s, Tc9s, Tc17s and Tc22s by ICS after a 6 hour re-stimulation. (d) % Lysis by polarized P14 Tc subsets after a 5 hour incubation with gp33 and AV control peptide pulsed EL4 cells. Results are means of technical replicates. (e) Polarized Tc subsets were stained for Granzyme B, Perforin, FasL and TRAIL. All FACs plots are gated on CD8+ T cells. Results are representative of at least 2-3 independent experiments.
Figure 5:
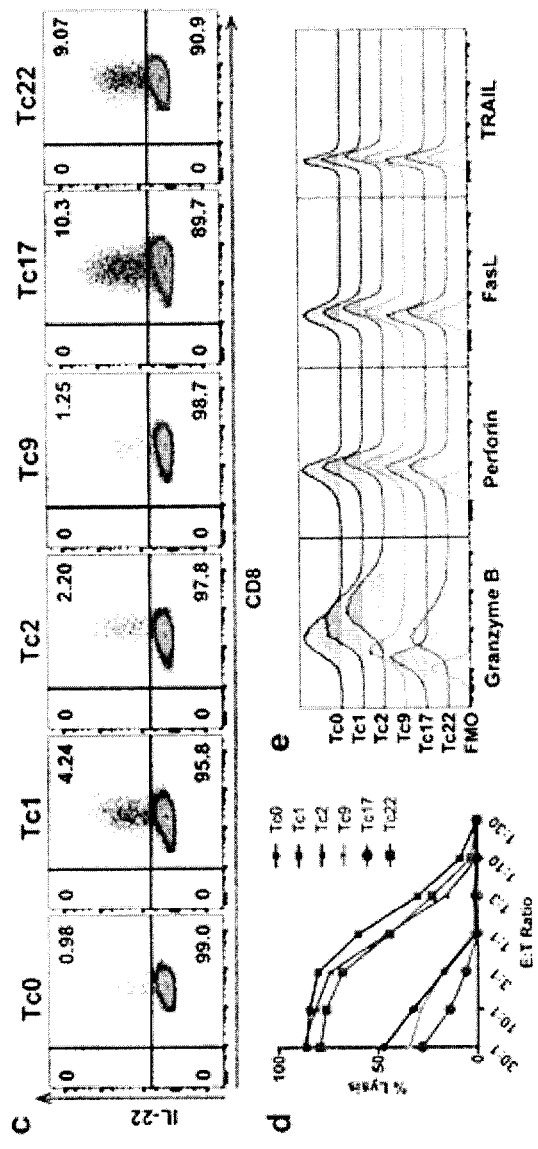
Figure 12:
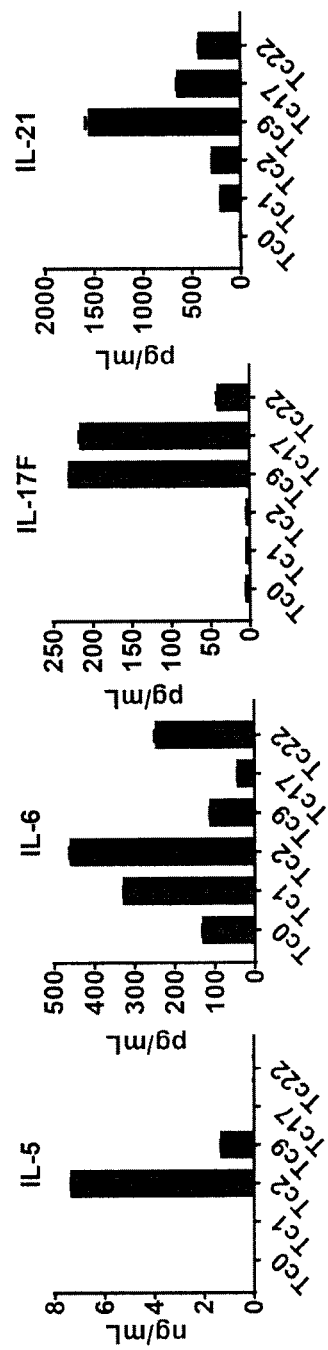
FIG. 12 shows cytokines produced by Tc subsets. (a-e) Day 3 polarized Tc subsets were washed and re-stimulated for 24 hours, and supernatants were collected and cytokine levels were quantified by cytometric bead array. Results are means of technical replicates±standard error.

We further characterized the cytokine expression profile of Tc22s and found the majority of IL-22 producers to be negative for IL-17 and IFN-γ, however some Tc22s also co-produced IFN-γ and to a lesser extent IL-17 (FIG. 5A). When comparing the cytokine expression profile of Tc22s against other Tc subsets, we observed a distinct profile produced by each Tc subset (FIG. 5B, FIG. 12). Tc22s were amongst the highest producers of IL-2 and TNF-α, while at the same time producing less IFN-γ than Tc0s and Tc1s. Tc22s also did not express the Th2/Tc2-associated cytokines IL-4, IL-5 and IL-13 nor the Th9/Tc9 lineage-defining cytokine IL-9. Tc22s also minimally expressed the Tc17 cytokines IL-17A and IL-17F. Interestingly, Tc9s and Tc17s both produced equally high levels of IL-17 although very few cells produced IL-17 in Tc9 conditions as detected by ICS (data not shown). This raises the possibility that Tc9s are converting to Tc17s during the overnight re-stimulation. Indeed, this phenomenon has been demonstrated in their CD4+counterparts, as IL-17 has been shown to be produced by Th9 cells after re-stimulation with anti-CD3[34], potentially due to the fact that IL-9 can act on CD4+ T cells to induce IL-17 production[35,36].

Although originally defined as a Th1-associated cytokine, subsequent studies have identified Th17s and Th22s as being prominent sources of IL-22[37]. Indeed, we demonstrate a similar finding in CD8+Tc subsets, as IL-22 is produced predominantly by Tc22s and Tc17s, and to a lesser extent by Tc1s (FIG. 5C). It is important to note that, on occasion, when using DCs to polarize the cells, IL-22 was sometimes detected in Tc0s, Tc2s and Tc9s to varying degrees, thereby suggesting undefined factors produced by DCs can promote some IL-22 expression in CD8+ T cells (FIG. 5C). Nevertheless, although other Tc subsets can produce IL-22 in some situations, Tc22s are amongst the highest producers.

An important part of CD8+ T cell effector function is their cytotoxic abilities. Our data suggests Tc1s, Tc2s and Tc22s are the most cytolytic, while Tc17s are poor killers (FIG. 5D). Cytolytic activity correlated with granzyme B production as Tc0, Tc1 Tc2, and Tc22 had moderate-high levels of granzyme B, while Tc9 and Tc17s were granzyme B low (FIG. 5E). All Tc subsets expressed low levels of perforin and FasL, and none of the Tc subsets expressed TRAIL (FIG. 5E).

Tc22 Polarized Cells Promote Tumor Regression

Figure 6:
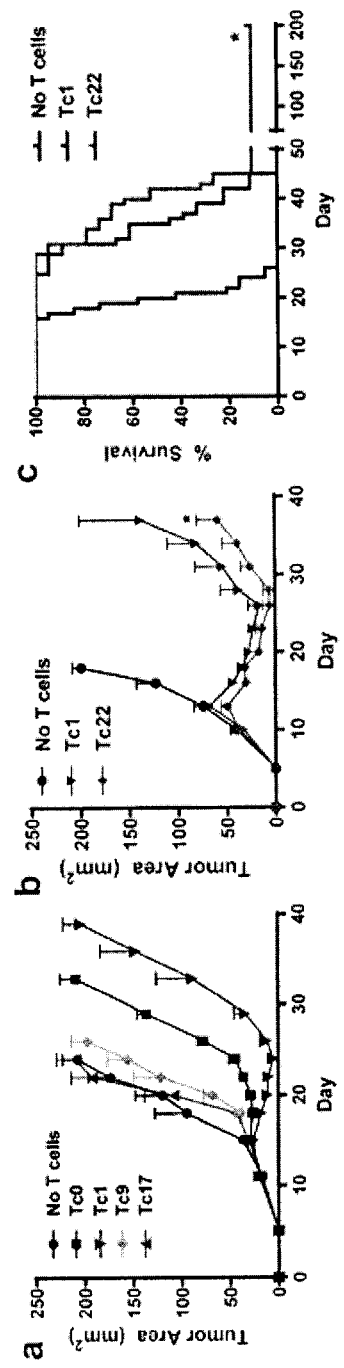
FIG. 6 shows Tc22s demonstrate potent anti-tumor function. (a-c) 8-12 week old mice were inoculated subcutaneously with $4 \times 10^5$ B16-gp33 tumor cells in the right flank and 10-11 days later received $1 \times 10^6$ polarized P14 Tc subsets. Results shown are mean tumor area (L×W) of (a) 5 or (b) 4 mice/group±standard error from one representative experiment. (c) Survival curve from (b) representing combined survival across all experiments (No T cells n=19, Tc1 n=18, Tc22 n=19). (d,e) Human CD8+ T cells were activated for 5 days in (d) non-polarizing conditions or (e) Tc22 conditions. (f) Cytokine production in tumor infiltrating CD8+ T cells expanded from an ovarian cancer patient. (g) % of IFN-γ+, IL-17+ or IL-22+CD8+ TILs expanded from ovarian cancer patients (n=17). (a-e) Results shown are representative of 2-5 independent experiments. *, p<0.05 between Tc1 and Tc22 as determined by repeated measures ANOVA with sidak test (b) or Log-Rank test (c).
Figure 6:
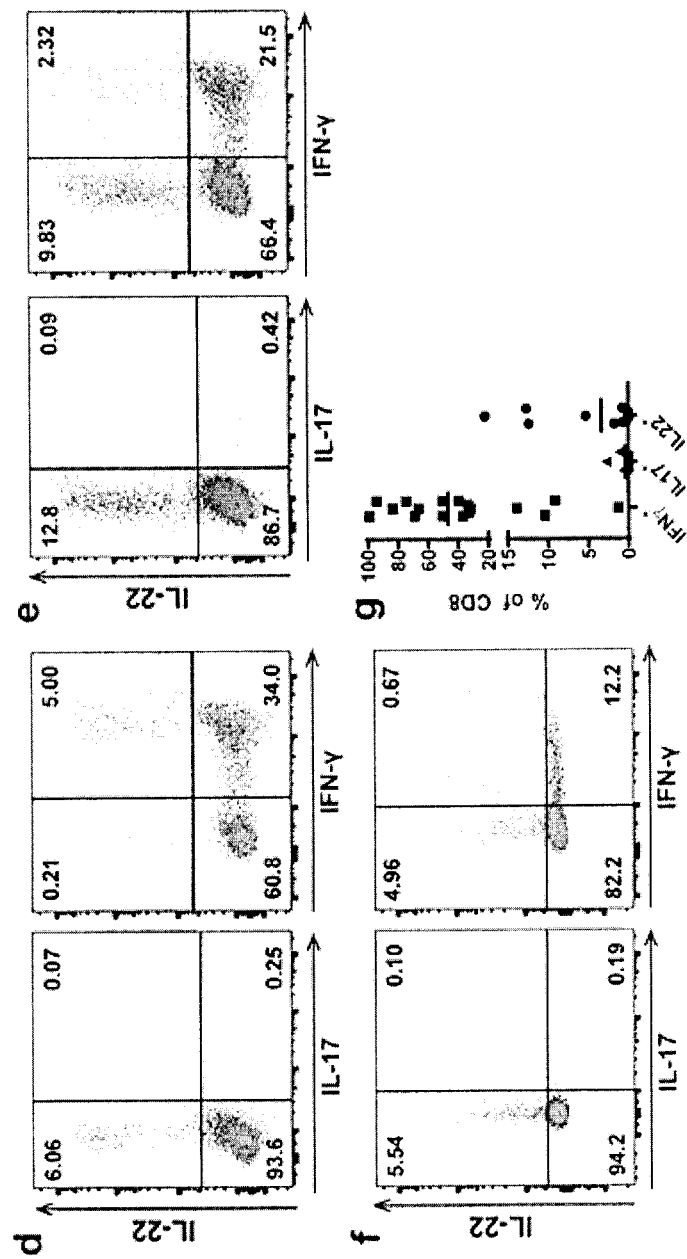

Having identified a differential cytolytic ability of the various Tc lineages, we evaluated the effector function of these cells in an in vivo experimental model. As the adoptive transfer of tumor specific CD8+ T cells has shown promising clinical results[38,39], we investigated whether polarizing the tumor-specific T cells to Tc22s and other Tc subsets prior to transfer may enhance antitumor functions. Several studies involving the transfer of tumor-specific T cells into mice bearing subcutaneous tumors have shown that Tc1s are superior to Tc2s[40,41] Given this, we set out to evaluate how Tc1s compare to other Tc subsets, namely Tc0s, Tc9s and Tc17s, in the context of our tumor model in which we transferred 1×10⁶ polarized CD8+ P14 T cells into mice bearing day 10-11 established B16-gp33 melanoma tumors (~5-6 mm in diameter). The greatest degree of protection was observed in mice that received Tc1s, as tumor progression was delayed by about 10 days longer than mice that received Tc0s (FIG. 6A). Unlike previous reports[6,10], we found that mice receiving Tc9s or Tc17s had virtually no protection against tumor growth. This is likely due to differences in the model used, as other studies have administered T cells in conjunction with supportive treatments including IL-2 injections, tumor-antigen vaccination and lymphodepletion, thereby providing more favorable conditions for response. Another possibility is that some of the previous studies demonstrating a role for Tc17s may actually be examining Tc22s instead, as there is a potential for Tc22 to be misidentified as Tc17 given that cells activated in Tc22 conditions can express IL-17 and RORγT to some degree (FIGS. 2A and 5B). Future studies may consider quantifying IL-22 production as well as IL-17 when polarizing Tc17s or evaluating Tc17 lineage commitment with markers identified here, such as 41BB−, OX40−, CD86+, CD101+ to rule this out.

In agreement with previously published studies[40-44], our model showed IL-12 induced Tc1 cells to have superior anti-tumor functions compared to previously described Tc subsets. Therefore, we performed multiple independent experiments to evaluate the anti-tumor functions of Tc22s using Tc1s as our reference Tc subset (FIG. 6B,C). Interestingly, we found that Tc22s performed at least as well as, if not better than, Tc1s. The growth of tumors in mice that received either Tc1s or Tc22s was arrested and tumors shrank in the majority of mice. On average, mice that received Tc22s had prolonged survival compared to those that received Tc1s (FIG. 6C). Surprisingly, in 2 out of 19 mice that received Tc22s, their tumors did not return. These mice demonstrated a complete response and remained tumor free for more than 200 days. From these experiments, it is clear that both Tc1s and Tc22s have superior anti-tumor properties.

To better understand the role of Tc22s in the context of human disease, we investigated whether Tc22s can be induced in human CD8+ T cells, and if so, could we detect them amongst tumor infiltrating lymphocytes (TILs). IL-22 producing CD8+ T cells were observed in activated PBMCs isolated from healthy donors (FIG. 6D). Upon activation in the presence of Tc22 polarizing cytokines, human CD8+ T cells skew primarily towards an IL-22+IL-17− IFN-γ− Tc22 phenotype, with the rest of the IL-22+ T cells co-producing IFN-γ+ (FIG. 6E). IL-22 producing CD8+ T cells were also detected in TILs expanded from ovarian cancer tissue of several patients, where they comprised up to ~22% of CD8+ T cells (FIG. 6F,G). Taken together, these findings indicate that human CD8+ T cells can polarize towards the Tc22 subset and can be detected in ovarian cancer TILs.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

1. Salgame, P. et al. Differing lymphokine profiles of functional subsets of human CD4 and CD8 T cell clones. *Science* (80-.). 254, 279-82 (1991).
2. Seder, R. A. et al. CD8+ T cells can be primed in vitro to produce IL-4. *J. Immunol.* 148, 1652-1656 (1992).
3. Sad, S., Marcotte, R. & Mosmann, T. R. Cytokine-induced differentiation of precursor mouse CD8+ T cells into cytotoxic CD8+ T cells secreting Th1 or Th2 cytokines. *Immunity* 2, 271-9 (1995).
4. Croft, M., Carter, L., Swain, S. L. & Dutton, R. W. Generation of polarized antigen-specific CD8 effector populations: reciprocal action of interleukin (IL)-4 and IL-12 in promoting type 2 versus type 1 cytokine profiles. *J. Exp. Med.* 180, 1715-1728 (1994).

5. Visekruna, A. et al. Tc9 cells, a new subset of CD8(+) T cells, support Th2-mediated airway inflammation. *Eur. J. Immunol.* 1-31 (2012). doi:10.1002/eji.201242825
6. Lu, Y. et al. Tumor-specific IL-9-producing CD8+Tc9 cells are superior effector than type-I cytotoxic Tc1 cells for adoptive immunotherapy of cancers. *Proc. Natl. Acad. Sci. U.S.A.* 111, 2265-70 (2014).
7. Intlekofer, A. M. et al. Anomalous type 17 response to viral infection by CD8+ T cells lacking T-bet and eomesodermin. *Science (80,).* 321, 408-11 (2008).
8. Hamada, H. et al. Tc17, a unique subset of CD8 T cells that can protect against lethal influenza challenge. *J. Immunol.* 182, 3469-81 (2009).
9. Huber, M. et al. A Th17-like developmental process leads to CD8(+) Tc17 cells with reduced cytotoxic activity. *Eur. J. Immunol.* 39, 1716-25 (2009).
10. Hinrichs, C. S. et al. Type 17 CD8+ T cells display enhanced antitumor immunity. *Blood* 114, 596-9 (2009).
11. Kryczek, I. et al. Cutting edge: Th17 and regulatory T cell dynamics and the regulation by IL-2 in the tumor microenvironment. *J. Immunol.* 178, 6730-3 (2007).
12. Yen, H.-R. et al. Tc17 CD8 T cells: functional plasticity and subset diversity. *J. Immunol.* 183, 7161-8 (2009).
13. Huber, M. et al. IL-17A secretion by CD8+ T cells supports Th17-mediated autoimmune encephalomyelitis. *J. Clin. Invest.* 123, 247-60 (2013).
14. Sheu, B. C. et al. Predominant Th2/Tc2 polarity of tumor-infiltrating lymphocytes in human cervical cancer. *J. Immunol.* 167, 2972-8 (2001).
15. Sabat, R., Ouyang, W. & Wolk, K. Therapeutic opportunities of the IL-22-IL-22R1 system. *Nat. Rev. Drug Discov.* 13, 21-38 (2013).
16. Weber, G. F. et al. IL-22-Mediated Tumor Growth Reduction Correlates with Inhibition of ERK1/2 and AKT Phosphorylation and Induction of Cell Cycle Arrest in the G2-M Phase. *J. Immunol.* 177, 8266-8272 (2006).
17. Zhang, F., Shang, D., Zhang, Y. & Tian, Y. Interleukin-22 suppresses the growth of A498 renal cell carcinoma cells via regulation of STAT1 pathway. *PLoS One* 6, e20382 (2011).
18. Lim, C. & Savan, R. The role of the IL-22/IL-22R1 axis in cancer. *Cytokine Growth Factor Rev.* 25, 257-271 (2014).
19. Huber, S. et al. IL-22BP is regulated by the inflammasome and modulates tumorigenesis in the intestine. *Nature* 491, 259-63 (2012).
20. Kryczek, I. et al. IL-22(+)CD4(+) T Cells Promote Colorectal Cancer Stemness via STAT3 Transcription Factor Activation and Induction of the Methyltransferase DOT1L. *Immunity* 40, 772-84 (2014).
21. Zenewicz, L. A. & Flavell, R. A. Recent advances in IL-22 biology. *Int. Immunol.* 23, 159-63 (2011).
22. Nograles, K. E. et al. IL-22-producing 'T22' T cells account for upregulated IL-22 in atopic dermatitis despite reduced IL-17-producing TH17 T cells. *J. Allergy Clin. Immunol.* 123, 1244-52.e2 (2009).
23. Res, P. C. M. et al. Overrepresentation of IL-17A and IL-22 producing CD8 T cells in lesional skin suggests their involvement in the pathogenesis of psoriasis. *PLoS One* 5, e14108 (2010).
24. Teraki, Y., Sakurai, A. & Izaki, S. IL-13/IL-22-coproducing T cells, a novel subset, are increased in atopic dermatitis. *J. Allergy Clin. Immunol.* 132, 971-974 (2013).
25. Oliveira, L. M. S. et al. Increased frequency of circulating Tc22/Th22 cells and polyfunctional CD38− T cells in HIV-exposed uninfected subjects. *Sci. Rep.* 5, 13883 (2015).
26. Jiang, R. et al. Interleukin-22 promotes human hepatocellular carcinoma by activation of STAT3. *Hepatology* 54, 900-9 (2011).
27. Zhang, S. et al. Increased Tc22 and Treg/CD8 ratio contribute to aggressive growth of transplant associated squamous cell carcinoma. *PLoS One* 8, e62154 (2013).
28. Liu, Y. et al. Interleukin-21 induces the differentiation of human Tc22 cells via phosphorylation of signal transducers and activators of transcription. *Immunology* 132, 540-8 (2011).
29. Duhen, T., Geiger, R., Jarrossay, D., Lanzavecchia, A. & Sallusto, F. Production of interleukin 22 but not interleukin 17 by a subset of human skin-homing memory T cells. *Nat. Immunol.* 10, 857-863 (2009).
30. Eyerich, S. et al. Th22 cells represent a distinct human T cell subset involved in epidermal immunity and remodeling. *J. Clin. Invest.* 119, 3573-85 (2009).
31. Zhu, J., Yamane, H. & Paul, W. E. Differentiation of effector CD4 T cell populations. *Annu. Rev. Immunol.* 28, 445-89 (2010).
32. Basu, R. et al. Th22 cells are an important source of IL-22 for host protection against enteropathogenic bacteria. *Immunity* 37, 1061-75 (2012).
33. Nakae, S., Iwakura, Y., Suto, H. & Galli, S. J. Phenotypic differences between Th1 and Th17 cells and negative regulation of Th1 cell differentiation by IL-17. *J. Leukoc. Biol.* 81, 1258-68 (2007).
34. Jäger, A., Dardalhon, V., Sobel, R. A., Bettelli, E. & Kuchroo, V. K. Th1, Th17, and Th9 effector cells induce experimental autoimmune encephalomyelitis with different pathological phenotypes. *J. Immunol.* 183, 7169-7177 (2009).
35. Elyaman, W. et al. IL-9 induces differentiation of TH17 cells and enhances function of FoxP3+ natural regulatory T cells. *Proc. Natl. Acad. Sci. U.S.A.* 106, 12885-12890 (2009).
36. Nowak, E. C. & Noelle, R. J. Interleukin-9 as a T helper type 17 cytokine. *Immunology* 131, 169-173 (2010).
37. Rutz, S., Eidenschenk, C. & Ouyang, W. IL-22, not simply a Th17 cytokine. *Immunol. Rev.* 252, 116-32 (2013).
38. Rosenberg, S. A. et al. Durable Complete Responses in Heavily Pretreated Patients with Metastatic Melanoma Using T-Cell Transfer Immunotherapy. Clin. *Cancer Res.* 17, 4550-4557 (2011).

39. Restifo, N. P., Dudley, M. E. & Rosenberg, S. A. Adoptive immunotherapy for cancer: harnessing the T cell response. *Nat. Rev. Immunol.* 12, 269-81 (2012).
40. Kemp, R. A. & Ronchese, F. Tumor-specific Tc1, but not Tc2, cells deliver protective antitumor immunity. *J. Immunol.* 167, 6497-502 (2001).
41. Helmich, B. K. & Dutton, R. W. The Role of Adoptively Transferred CD8 T Cells and Host Cells in the Control of the Growth of the EG7 Thymoma: Factors That Determine the Relative Effectiveness and Homing Properties of Tc1 and Tc2 Effectors. *J. Immunol.* 166, 6500-6508 (2001).
42. Nishimura, F. et al. Adoptive transfer of type 1 CTL mediates effective anti-central nervous system tumor response: critical roles of IFN-inducible protein-10. *Cancer Res.* 66, 4478-87 (2006).
43. Garcia-Hernandez, M. D. L. L. et al. Adoptive transfer of tumor-specific Tc17 effector T cells controls the growth of B16 melanoma in mice. *J. Immunol.* 184, 4215-4227 (2010).
44. Yu, Y. et al. Adoptive transfer of Tc1 or Tc17 cells elicits antitumor immunity against established melanoma through distinct mechanisms. *J. Immunol.* 190, 1873-81 (2013).
45. Pircher, H., Bürki, K., Lang, R., Hengartner, H. & Zinkernagel, R. M. Tolerance induction in double specific T-cell receptor transgenic mice varies with antigen. *Nature* 342, 559-561 (1989).
46. Dissanayake, D. et al. Nuclear factor-KB1 controls the functional maturation of dendritic cells and prevents the activation of autoreactive T cells. *Nat. Med.* 17, 1663-7 (2011).
47. Kim, D. et al. TopHat2: accurate alignment of transcriptomes in the presence of insertions, deletions and gene fusions. *Genome Biol.* 14, R36 (2013).
48. Langmead, B., Trapnell, C., Pop, M. & Salzberg, S. L. Ultrafast and memory-efficient alignment of short DNA sequences to the human genome. *Genome Biol.* 10, R25 (2009).
49. DeLuca, D. S. et al. RNA-SeQC: RNA-seq metrics for quality control and process optimization. *Bioinformatics* 28, 1530-1532 (2012).
50. Li, H. et al. The Sequence Alignment/Map format and SAMtools. *Bioinformatics* 25, 2078-9 (2009).
51. Trapnell, C. et al. Transcript assembly and quantification by RNA-Seq reveals unannotated transcripts and isoform switching during cell differentiation. *Nat. Biotechnol.* 28, 511-515 (2010).
52. R: A language and environment for statistical computing. (2015). Available at: https://www.r-project.org/.
53. Trapnell, C. et al. Differential gene and transcript expression analysis of RNA-seq experiments with TopHat and Cufflinks. *Nat. Protoc.* 7, 562-578 (2012).
54. Crome, S. Q. et al. A distinct innate lymphoid cell population regulates tumor-associated T cells. *Nat. Med.* 1-10 (2017). doi:10.1038/nm.4278

The invention claimed is:

1. A method for inducing Tc22 lineage T cells from a population of $CD8^+$ T cells, the method comprising:

a) providing a population of $CD8^+$ T cells;

b) activating the population of $CD8^+$ T cells by culturing or contacting the population with at least one of (i) anti-CD3 antibody and (ii) gp33 peptide consisting of the amino acid sequence set forth in SEQ ID NO. 1; and c) culturing or contacting the population of $CD8^+$ T cells with IL-6 and wherein the Tc22 lineage T cells are $CD8^+$/IL−$22^+$/$IL17^-$/$IFN\gamma^{low}$.

2. The method of claim 1, wherein the population of $CD8^+$ T cells is additionally cultured or contacted with TNF-α.

3. The method of claim 1, wherein the population of $CD8^+$ T cells is additionally cultured or contacted with an aryl hydrogen receptor (AhR) agonist.

4. The method of claim 1, wherein the population of $CD8^+$ T cells is additionally cultured or contacted with anti-IFNγ antibody.

5. The method of claim 1, wherein the population of $CD8^+$ T cells is additionally cultured or contacted with anti-TGF-β antibody.

6. The method of claim 1, wherein the population of $CD8^+$ T cells is additionally cultured or contacted with IL-21.

7. The method of claim 1, wherein the population of $CD8^+$ T cells is additionally cultured or contacted with IL-23.

8. The method of claim 1, wherein the Tc22 lineage T cells are additionally IL-$4^-$, IL-$5^-$, IL-$9^-$, IL-$10^-$and/or or IL-$13^-$.

9. The method of claim 8, wherein the Tc22 lineage T cells are additionally TNF-$\alpha^{hi}$ and/or IL-$2^{hi}$.

10. The method of claim 1, wherein step c) is performed before or after step b).

11. The method of claim 1, wherein step c) is performed simultaneously with step b).

12. The method of claim 3, wherein the an aryl hydrogen receptor (AhR) agonist is 6-Formylindolo(3,2-b)carbazole (FICZ).

\* \* \* \* \*

```
                              SEQUENCE LISTING

<160> NUMBER OF SEQ ID NOS: 1

<210> SEQ ID NO 1
<211> LENGTH: 9
<212> TYPE: PRT
<213> ORGANISM: Lymphocytic choriomeningitis virus

<400> SEQUENCE: 1

Lys Ala Val Tyr Asn Phe Ala Thr Met
1               5
```